(12) United States Patent
Arisawa et al.

(10) Patent No.: US 9,175,004 B2
(45) Date of Patent: Nov. 3, 2015

(54) CATALYST PRECURSOR, METHOD FOR PRODUCING THE SAME, METHOD FOR USING THE SAME, AND REACTOR THAT USES THE SAME

(75) Inventors: Mitsuhiro Arisawa, Sapporo (JP); Satoshi Shuto, Sapporo (JP); Naoyuki Hoshiya, Tokyo (JP)

(73) Assignees: NATIONAL UNIVERSITY CORPORATION HOKKAIDO UNIVERSITY (JP); FURUYA METAL CO., LTD. (JP)

( * ) Notice: Subject to any disclaimer, the term of this patent is extended or adjusted under 35 U.S.C. 154(b) by 730 days.

(21) Appl. No.: 13/384,281

(22) PCT Filed: Jul. 16, 2010

(86) PCT No.: PCT/JP2010/062065
§ 371 (c)(1),
(2), (4) Date: Jan. 16, 2012

(87) PCT Pub. No.: WO2011/010610
PCT Pub. Date: Jan. 27, 2011

(65) Prior Publication Data
US 2012/0115714 A1 May 10, 2012

Related U.S. Application Data

(66) Substitute for application No. PCT/JP2010/062065, filed on Jul. 16, 2010.

(30) Foreign Application Priority Data

Jul. 21, 2009 (JP) .................................. 2009-170507

(51) Int. Cl.
| | |
|---|---|
| B01J 23/52 | (2006.01) |
| B01J 31/28 | (2006.01) |
| C07D 491/113 | (2006.01) |
| B01J 27/04 | (2006.01) |
| B01J 35/00 | (2006.01) |
| B01J 35/04 | (2006.01) |
| B01J 35/06 | (2006.01) |
| B01J 37/02 | (2006.01) |
| B01J 37/20 | (2006.01) |
| C07C 1/32 | (2006.01) |
| C07C 17/263 | (2006.01) |
| C07C 41/30 | (2006.01) |
| C07C 231/12 | (2006.01) |
| B01J 23/44 | (2006.01) |

(52) U.S. Cl.
CPC ............ *C07D 491/113* (2013.01); *B01J 23/52* (2013.01); *B01J 27/04* (2013.01); *B01J 35/002* (2013.01); *B01J 35/04* (2013.01); *B01J 35/06* (2013.01); *B01J 37/0207* (2013.01); *B01J 37/0209* (2013.01); *B01J 37/0225* (2013.01); *B01J 37/20* (2013.01); *C07C 1/321* (2013.01); *C07C 17/263* (2013.01); *C07C 41/30* (2013.01); *C07C 231/12* (2013.01); *B01J 23/44* (2013.01); *C07C 2523/44* (2013.01); *C07C 2523/52* (2013.01)

(58) Field of Classification Search
None
See application file for complete search history.

(56) References Cited

U.S. PATENT DOCUMENTS

| 7,122,848 B2 * | 10/2006 | Nishida et al. ................. 257/184 |
| 2005/0182214 A1 | 8/2005 | Nishida et al. |

FOREIGN PATENT DOCUMENTS

| EP | 1552884 A1 | 7/2005 |
|---|---|---|
| JP | 2000-290099 A | 10/2000 |
| JP | 2001-192874 A | 7/2001 |
| JP | 2002-53312 A | 2/2002 |
| JP | 2004-130258 A | 4/2004 |
| JP | 2004-188390 * | 7/2004 |
| JP | 2004-188390 A | 7/2004 |
| JP | 2005-270918 A | 10/2005 |
| JP | 2007-54790 A | 3/2007 |
| JP | 2007-266477 A | 10/2007 |
| JP | 2007-332441 A | 12/2007 |
| WO | 2004/033093 A1 | 4/2004 |
| WO | 2007/023942 A1 | 3/2007 |

OTHER PUBLICATIONS

Sulfur Modifaction of Au Via Treament With Piranha Solution Provides Low- Pd Releasing and Recyclable Pd Material, SAPd. By Naoyuki Hoshiya et al. JACS pubhished on Web May 2010.*
Extended European Search Report for Application No. 10802230.2; Date of Mailing: Jul. 8, 2013; 11 pgs.
"Hard x-ray photoemission spectroscopic investigation of palladium catalysts immobilized on a GaAs(001) surface"; Journal of Applied Physics, American Institute of Physics, New York, US, vol. 108, No. 2, Jul. 27, 2010; pp. 24309-24309; XP012142385; ISSN: 0021-8979; DOI: 10.1063/1.3456507 the whole document More particularly from third page, right hand column: "C. S 1s photoemission". 18 pgs.

(Continued)

*Primary Examiner* — Patricia L Hailey
*Assistant Examiner* — Colette Nguyen
(74) *Attorney, Agent, or Firm* — Cantor Colburn LLP

(57) ABSTRACT

The present invention provides the catalyst precursor that has excellent safety and stability, has high stable activity retention rate, can be recycled, increases yield resulted from a reaction, and is easily processed into various forms. The catalyst precursor comprises a structure in which the entire structure is composed of gold or a gold-based alloy and the surface of the structure is modified with elemental sulfur, or at least the surface of the structure is composed of gold or a gold-based alloy and the surface of the structure is modified with elemental sulfur, and a catalytic metal compound supported on the structure, wherein the catalyst precursor has peaks derived from the catalytic metal compound and also sulfur as analyzed by photoelectron spectroscopy, and wherein the peak derived from sulfur is of the sulfur 1s orbital observed within a range of 2470 eV±2 eV in terms of the peak top position.

12 Claims, 2 Drawing Sheets

(56) References Cited

OTHER PUBLICATIONS

International Search Report for International Application No. PCT/ "Sulfur Modification of Au via Treatment with Piranha Solution Provides Low-Pd Releasing and Recyclable Pd Material, SAPd"; Authors: Naoyuki Hoshiya et al.; Journal of American Chemical Society, vol. 132, May 12, 2010; pp. 7270-7272; XP002699580; DOI: 10.1021/ja9100084 the whole document Published in Internet on May 12, 2010; 5 pgs. JP2010/062065, mailed Oct. 19, 2010 with English translation.

C. Baleizao et al., "Oxime Carbapalladacycle Covalently Anchored to High Surface Area Inorganic Supports or Polymers as Heterogeneous Green Catalysts for the Suzuki Reaction in Winter", J. Org. Chem. 2004, 69, 439-446.

A. Corma et al., "A periodic mesoporous organosilica containing a carbapalladacycle complex as heterogeneous catalyst for Suzuki cross-coupling", Journal of Catalysis. 229 (2005) 322-331.

I. Davies, et al. "Are Heterogeneous Catalystcs Precursors to Homogeneous Catalysts", J. Am. Chem. Soc. 2001, 123, 10139-10140.

C.E. Garrett, K. Prasad, "The Art of Meeting Palladium Specifications in Active Pharmaceutical Ingredients Produced by Pd-Catalyzed Reaction", Adv. Synth. Catal. 2004, 346, 889-900.

B.H. Lipshutz et al., "On the Nature of the 'Heterogeneous' Catalyst: Nickel-on-Charcoal", J. Org. Chem., 2003, 68, 1177-1189.

N.T.S. Phan, et al. "On the Nature of the Active Species in Palladium Catalyzed Mizoroki-Heck and Suzuki-Miyaura Couplings—Homogeneous or Heterogeneous Catalysis, A Critical Review", Adv. Synth. Catal. 2006, 348, 609-679.

J.M. Richardson et al. "Strong evidence of solution-phase catalysis associated with palladium leaching from immobilized thiols during Heck and Suzuki coupling of aryl iodides, bromides, and chlorides", Journal of Catalysis. 251 (2007) 80-93.

L. Yin et al., "Carbon-Carbon Coupling Reactions Catalyzed by Heterogeneous Palladium Catalysts", Chem. Rev. 2007, 107, 133-173.

* cited by examiner

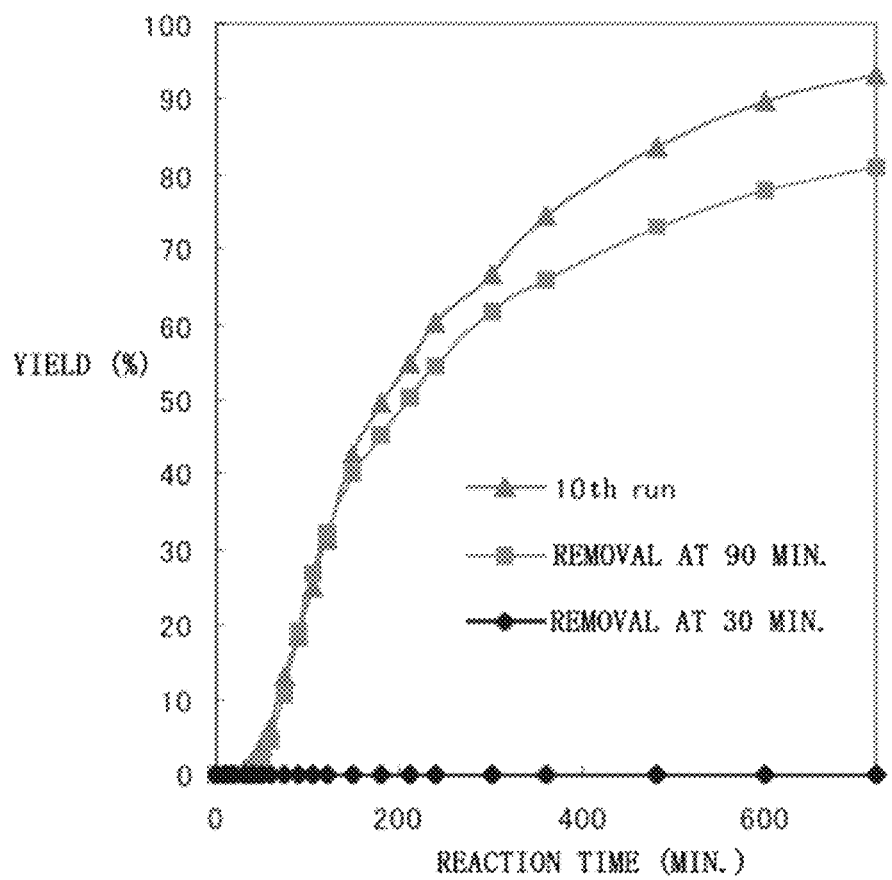

US 9,175,004 B2

CATALYST PRECURSOR, METHOD FOR PRODUCING THE SAME, METHOD FOR USING THE SAME, AND REACTOR THAT USES THE SAME

CROSS REFERENCE TO RELATED APPLICATIONS

This is a U.S. National Stage of Application No. PCT/JP2010/062065, filed on Jul. 16, 2010. Priority under 35 U.S.C. §119 (a) and 35 U.S.C. §365(b) is claimed from Japanese Application No. 2009-170507, filed Jul. 21, 2009, the disclosure of which is also incorporated herein by reference.

TECHNICAL FIELD

The present invention relates to a catalyst precursor that is a sulfur modified gold structure-supported metal compound having a composition of three components "gold-sulfur-catalytic metal" in which a catalytic metal compound is supported on the gold surface modified with sulfur, a method for producing the same, a method for using the same, and a reactor using the same.

BACKGROUND ART

Chemistry of organometallic complex enables to readily construct new bonds between carbon and carbon or carbon and hetero atom, and is widely used in various chemical fields including drug discovery and organic synthesis. The present inventors have devoted adequate effort to development of novel reactions and synthesis of bioactive compounds using organometallic complexes such as of ruthenium, palladium, and rare earth metal ytterbium, and have reported findings.

Reactions using an organometallic complex however have the major issue of removal of trace metals remaining in a reaction product after the reaction, as well as a problem in stability of the organometallic complex. The issue should be solved urgently particularly in the field of fine chemical for producing pharmaceuticals and electronic components, because the trace metals are harmful to humans and impair expected product's function (see, for example, Non-Patent Document 1). In addition, considering to the recent high social demand for the development of environment-conscious process, use of organometallic complexes in industrial scale has many problems in efficiency and recovery of a metal in a catalyst used and treatment of waste solution containing a metal, as well as the issue of removal of trace metals remaining in a reaction product.

One of the solutions to these problems of organometallic complexes is of supporting an organometallic complex to a solid support. Various solid-supported organometallic catalysts have been developed. Among these catalysts, activated charcoal, resins, or polymers or the like is commonly used as a solid support (see, for example, Non-Patent Documents 2 and 3). However, conventional solid-supported organometallic catalysts using these solid supports still leak trace amounts of metals from the supports. Further, in some solid-supported catalysts using resins or polymers as a solid support, a product and the like may be adsorbed on the solid support and thus the product may be difficult to be recovered efficiently. Now, in the field of solid-support catalyst, there is a demand for developing a solid support and a supporting method alternative to the conventional supports and methods. Under this circumstance, the present inventors have investigated to fix a catalyst metal more firmly by constructing a three-component structure of "semiconductor-sulfur-metal." In other words, the present inventors have tried to develop a new catalyst having improved stability, leaking less amount of metals, and exhibiting reusable catalytic activity by modifying the surface of a substrate such as semiconductor, metal, or insulator with sulfur as a coupler and fixing an organometallic complex with the sulfur. As a result, the present inventors have found that a gallium arsenide (001) substrate modified with sulfur at the surface of the substrate can support an organometallic complex and that an amount of metals leaked from the organometallic complex is very smaller than that from an organometallic complex bonded to a conventional solid support in the Mizorogi-Heck reaction (see, for example, Patent Documents 1 to 3).

PRIOR ART DOCUMENTS

Patent Document

Patent Document 1: JP-A2004-130258
Patent Document 2: JP-A2005-270918
Patent Document 3: JP-A2007-54790
Patent Document 4: JP-A2007-266477
Patent Document 5: JP-A2002-53312
Patent Document 6: JP-A2001-192874
Patent Document 7: JP-A2007-332441

Non-Patent Document

Non-Patent Document 1: C. E. Garrett, K. Prassad, Adv. Synth. Catal. 346, 889, (2004)
Non-Patent Document 2: N. T. S. Plan, M. Van Der Slyus, C. W. Jones, Adv. Synth. Catal, 348, 609, (2006)
Non-Patent Document 3: L. Yin, J. Liebsher, Chem. Rev. 107, 133, (2007)
Non-Patent Document 4: I. Davies, L. Matty, D. L. Hughes, P. J. Reider, J. Am. Chem. Soc. 2001, 123, 10139.
Non-Patent Document 5: B. H. Lipshutz, S. Tasler, W. Chrisman, B. pliethoff, B. Tecsche, J. Org. Chem. 2003, 68, 1177.
Non-Patent Document 6: C. Baleizao, A. Corma, H. Garcia, A. Leyva, J. Org. Chem. 2004, 69, 439.
Non-Patent Document 7: A. Corma, D. Das, H. Garcia, A. Leyva, J. Catal. 2005, 229, 322.
Non-Patent Document 8: J. M. Richardson, C. W. Jones, J. Catal. 2007, 251, 80.

DISCLOSURE OF THE INVENTION

Problems to be Solved by the Invention

The sulfur modified gallium arsenide substrate-supported catalyst prepared by modifying the surface of the gallium arsenide (001) substrate with sulfur and bonding an organometallic complex to the substrate could be recycled in the Mizorogi-Heck reaction, which is a catalytic organic synthesis, and leaked metals from the substrate in an incomparably small amount than that from conventional solid-supported organometallic catalysts. Further, since the catalyst was in a plate form, the surface of the catalyst could be easily washed with a solution, enabling to very simple recovery of a product and the like. The sulfur modified gallium arsenide-supported catalyst however resulted low yields in other catalytic organic syntheses such as the Suzuki-Miyaura coupling and was difficult to be recycled. Further, since the solid support of the sulfur modified gallium arsenide-supported catalyst contains toxic arsenic, there is a concern about safety of the catalyst for using in the field of fine chemical widely employing organometallic catalysts for producing pharmaceuticals and electronic material syntheses. The solid support also has disadvantages of low physical strength, fragility, and sensitivities to humidity and acid, and is hard to be handled. According to these problems including strength, for some raw materials for reacting, the catalyst could not maintain high yield and resulted a decreasing yield with recycling in reactions. Furthermore, the sulfur modified gallium arsenide-supported catalyst was hard to be processed in to a desired form, and was not suitable for introduction into a synthesizing apparatus.

Problems of the sulfur modified gallium arsenide-supported catalyst also can be seen in Patent Documents 1 to 3. Patent Document 1 discloses a substrate on the surface of which sulfur atoms are deposited and then an organometallic complex is bonded. Examples of the organometallic complex described in the patent include catalytically active metal complexes such as of ruthenium, palladium, and rare earth metal ytterbium. Specific examples include phosphine palladium complexes such as tetrakis triphenylphosphine palladium (Pd (PPh$_3$)$_4$). The patent discloses that effective reactions of the catalyst include carbon-carbon bonding, hydrogen reduction, asymmetric synthesis, and substitution. Examples of the substrate on which sulfur atoms are deposited include semiconductor substrates such as a gallium arsenide substrate, metal substrates such as gold, and resin substrates such as a synthetic resin. However, Examples only showed about the Mizorogi-Heck reaction using a gallium arsenide (GaAs) plate catalyst. For other substrates, there was only suggestion for the possibility.

Patent Document 2 discloses a metal catalyst similarly produced as in Patent Document 1 by bonding or adsorbing molecules or atoms on the surface of a substrate and bonding or adsorbing an organometallic complex to the molecules or atoms. In this patent, examples of the form of the metal catalyst described include a plate form, a cylindrical form, and a mesh form. Examples of the substrate described in the patent include gold. However, Examples only showed about the Mizorogi-Heck reaction using a Ga—As plate catalyst. The gold substrate was not confirmed in fact.

Patent Document 3 discloses a method for producing a substrate having a metal compound bonded on the surface thereof, comprising fixing sulfur atoms on the surface of the substrate, bonding further the metal compound on the surface of the substrate, and heating the substrate in an organic solvent. In Example 10, the patent describes that a gold thin film could be used as a substrate, and that a substrate-bonded catalyst produced by immersing a gold thin film in a solution of Pd(dba)$_2$ and heating maintained its activity retention rate by 30 to 80% after recycled 10 times in the Mizorogi-Heck reaction. The catalyst however was inferior to a Ga—As plate catalyst and was impractical. In addition, while the gold structure-supported metal compound of the present invention functions as a "catalyst precursor" as shown in Examples described below, the substrate-bonded catalyst of Example 10 in Patent Document 3 is supposed as not functioning as a catalyst precursor in view of activity retention rate.

Use of gold as a substrate is preferred from the viewpoint of safety as described above. However, as described above, Patent Documents 1 to 3 suggested only the possibility of use of gold substrate. A gold substrate was really inferior in performances to the Ga—As plate substrate, and a reason was unknown. The Ga—As plate substrate also could not solve the problems of the sulfur modified gallium arsenide substrate-bonded organometallic complex.

The present invention is directed to solve the problems described above. More specifically, the present invention is to provide a catalyst precursor having excellent safety and stability, having high stable activity retention rate, can be recycled, resulting high yield, and being easily processed into various forms.

None of Patent Documents 1 to 3 discloses a "catalyst precursor" similarly as the sulfur modified gold-supported catalyst precursor of the present invention, although these patent disclose a "catalyst". As used herein, the "catalyst precursor" exhibits no catalytic activity by itself or only by being immersed in a solution. The "catalyst precursor" releases a catalytically active species only after used in an intended reaction, or is a donor of the catalytically active species (for example, when the catalytically active species is palladium, "Pd reservoir" or "Pd container"). The catalytically active species really exerts a catalytic activity (see, FIG. 2). In the present invention, the catalytically active species is soluble.

As the result of extensive investigation to solve the problems, the present inventors have found a catalyst precursor that can gradually release a catalytically active species exhibiting a catalytic performance superior to that of the gallium arsenide substrate-bonded organometallic complex through use of gold, which has low toxicity and favorable processability, as a solid support and of different modification mode of the gold substrate with sulfur from the conventional technique, and accomplished the present invention. Specifically, the catalyst precursor according to the present invention comprises a structure in which the entire structure or at least the surface of the structure is composed of gold or a gold-based alloy and the surface of the structure is modified with elemental sulfur, and comprises a catalytic metal compound supported on the structure. The catalyst precursor is characterized by having peaks derived from the catalytic metal compound and also sulfur as analyzed by photoelectron spectroscopy, wherein the peak derived from sulfur is of the sulfur is orbital observed within a range of 2470 eV±2 eV in terms of the peak top position. In one embodiment of the catalyst precursor according to the present invention, the peak of the sulfur is orbital is observed as a single peak.

The catalyst precursor according to the present invention is characterized by comprising a structure in which the entire structure or at least the surface of the structure is composed of gold or a gold-based alloy and the surface of the structure is treated with a solution containing Caro's acid, and comprising a catalytic metal compound supported on the surface-treated structure.

In one embodiment of the catalyst precursor according to the present invention, the solution containing Caro's acid is a solution containing a sulfur-containing acid and an oxidizer, a solution electrochemically-oxidized a sulfur-containing acid, or a solution containing a persulfate and sulfuric acid.

In one embodiment of the catalyst precursor according to the present invention, the surface of the structure treated with the solution on the surface is modified with elemental sulfur, and the catalyst precursor has peaks derived from the catalytic metal compound and also sulfur as analyzed by photoelectron spectroscopy, wherein the peak derived from sulfur is of the sulfur is orbital observed within a range of 2470 eV±2 eV in terms of the peak top position.

In the catalyst precursor according to the present invention, the catalytic metal compound is a metal salt or metal complex containing at least one selected from ruthenium, rhodium, iridium, palladium, and platinum.

In the catalyst precursor according to the present invention, the structure preferably has a form selected from plate, mesh, cylinder, coil, particle, and combinations thereof. Although the GaAs (001) plate substrate has a disadvantage of small surface area available for supporting, the present invention can expand the surface of the solid support due to use of gold having good processability. As a result, the reaction yield can be easily increased.

In the catalyst precursor according to the present invention, the structures are preferably plural combined to form a three-dimensional structure. For example, the catalyst precursors can form a reaction tank, a stirring bar, an agitating blade, and the like, resulting in an increased reaction yield.

The method for producing the catalyst precursor according to the present invention comprises steps of surface-treating by immersing a structure in a solution containing Caro's acid wherein the entire structure or at least the surface of the structure is composed of gold or a gold-based alloy and a supporting step of supporting by bonding or adsorbing a catalytic metal compound to the surface of the structure.

In one embodiment of the method for producing the catalyst precursor according to the present invention, the solution containing Caro's acid is a solution containing a sulfur-containing acid and an oxidizer, a solution electrochemically-oxidized a sulfur-containing acid, or a solution containing a persulfate and sulfuric acid.

In the method for producing the catalyst precursor according to the present invention, the solution containing Caro's acid is preferably piranha solution. The solution enables to clean the surface of the gold support and simultaneously modify the surface with sulfur in a high grade state.

The method for using the catalyst precursor according to the present invention comprises immersing the catalyst precursor in a solution containing a halogenated hydrocarbon compound as a raw material or apart of raw materials to release a catalytically active species from the catalyst precursor.

The intermolecular or intramolecular reaction for forming a carbon-carbon bond according to the present invention uses the catalyst precursor according to the present invention.

The intermolecular or intramolecular reaction for forming a carbon-nitrogen bond according to the present invention uses the catalyst precursor according to the present invention.

The intermolecular or intramolecular reaction for forming a carbon-oxygen bond according to the present invention uses the catalyst precursor according to the present invention.

The method for using the catalyst precursor according to the present invention is characterized by that the catalyst precursor according to the present invention is a structure in a mesh form, the structure is immersed in a reaction solution of a reactant in a solvent, and the reaction solution is mechanically stirred so as to form flows of the reaction solution along with the surface of the structure and passing through the mesh thereof to progress the reaction.

The reactor according to the present invention comprises the catalyst precursor according to the present invention attached to a reaction part.

Effect of the Invention

The catalyst precursor according to the present invention has excellent safety and stability, has high stable activity retention rate, can be recycled, results high yield, and is easily processed into various forms. According to the present invention, a solid-supported catalyst precursor has been successfully developed, that has both a high activity and an ability of recycling and uses a solid support with a lower toxicity. The sulfur-modified gold-supported catalyst precursor according to the present invention can be recycled in the Suzuki-Miyaura coupling, the Mizorogi-Heck reaction, the Sonogashira coupling, the Stille coupling, and the Buchwald-Hartwig coupling, and leaks a metal species into a reaction solution at the world's lowest level. Particularly in the Suzuki-Miyaura coupling, in which conventional gallium arsenide-supported catalysts are hard to develop the reaction, the catalyst precursor according to the present invention can be recycled. For example, the structure in a mesh form could be recycled thirty times with an average yield of not less than 90%. In the reaction, an amount of Pd leaked in a reaction solution was 7 to 1 ppb, which was several orders of magnitude less than 280 to 40 ppb in cases of gallium arsenide-supported catalysts. In reactions of raw materials resulting in decreasing yields with recycling gallium arsenide-supported catalysts, the catalyst precursor according to the present invention can be recycled without decreasing yields. In such recycle of the catalyst precursor, a product can be easily separated from the catalyst precursor by washing the surface with a solution or the like. In washing, the catalyst precursor according to the present invention showed almost no deterioration. In addition, the catalyst precursor according to the present invention employs a gold material having good processability as a solid support, and can be easily processed into a different form. There were also findings that the support may be gilded, and that other catalyst metals than Pd can be applied. As described above, use of the catalyst precursor according to the present invention can solve the problems of conventional supported catalysts including an amount of leaked metals from the catalyst and separation of a product from the catalyst and the problems of gallium-arsenide-supported catalysts including toxicity, durability, and processability of the solid support.

BRIEF DESCRIPTION OF THE DRAWINGS

FIG. 3 shows a graph of product yield variations per hour for cases of removal of the sulfur modified gold-supported catalyst precursor according to the Example described below from the reaction system at different times.

MODE FOR CARRYING OUT THE INVENTION

Figure 1:
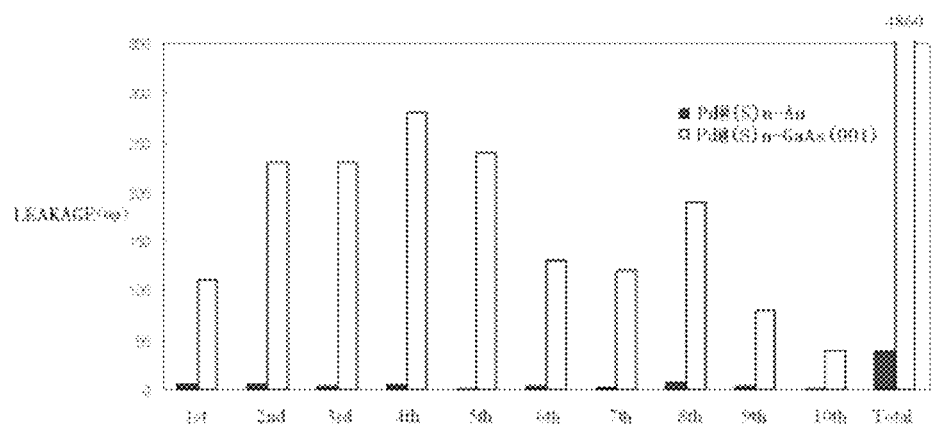
FIG. 1 shows a graph showing a comparison between an amount of Pd leaked of the sulfur modified gold-supported catalyst precursor according to Example described below (in a mesh form) and the same of the gallium-arsenide-supported catalyst of Comparative Example 2.

Below, the present invention will be described in detail with literature to embodiments, but should not be interpreted as being limited by the description. Embodiments can be varied with any modification within the range that does not impair the effects of the present invention.

(Solid Support)

The gold solid support of the present invention is a structure in which the entire structure is composed of gold or a gold-based alloy or at least the surface of the structure is composed of gold or a gold-based alloy. Specific examples of the form of the structure include a plate, mesh, cylindrical, coil, or particulate form, or combinations thereof. The gold structure is only necessary to be coated over the surface with a gold-containing substance. For example, in cases of the gold structure being in a mesh form, the gold structure may be a gilded mesh preferably made of Cu or stainless-steel, or of nonmetal materials such as plastics and carbon fibers. The gold structure is more preferably made of fine gold mesh. For coating with gold, known methods of film formation can be employed, including plating and deposition. Examples of the gold-based alloy include a gold-palladium alloy. A mesh material can have any wire diameter and opening. The mesh material preferably has a wire diameter of 2 mm to 0.0016 mm and an opening of 10.7 mm to 0.0159 mm, and more preferably a wire diameter of 0.34 mm to 0.06 mm and an opening of 0.93 to 0.108 mm.

(Three-Dimensional Structure)

The catalyst precursor of the present invention can be in any form as long as it can contact with an organic compound. For example, the catalyst precursor may be in a stereoscopic form by being adhered to a stirring bar or the like, or may be combined with other catalyst precursors to form a three-dimensional construction such as an agitating blade. Use of the stirring bar or the agitating blade by itself is the method of reacting. There is also a possible method of reacting by filling a cylindrical vessel with the catalyst precursor and passing an organic compound through the vessel. An example of the methods of reacting comprises immersing the structure constructed with the catalyst precursor in a reaction solution of a reactant in a solvent, and mechanically stirring the reaction solution so as to form flows along with the surface of the structure and passing through the mesh to progress the reaction. The reactor is only necessary to be equipped with the catalyst precursor at a reaction part.

(Catalytic Metal Compound)

Any metal element can be employed for the catalytic metal compound fixed on the support of the present invention as long as it has activities in reactions for organic synthesis, preferably for forming a new bond, and more preferably for forming a new carbon-carbon, carbon-nitrogen, or carbon-oxygen bond. Preferred are transition metals. Specific examples of the transition metal include ruthenium, rhodium, iridium, palladium, and platinum. Among these metals, the metal having higher affinity for a sulfur atom is more preferred. Particularly preferred metal element is palladium. Examples of the catalytic metal compound include inorganic salts such as hydrochlorides, sulfates, and nitrates, organic acid salts such as acetates and lactates, and metal complexes such as phosphine, acetylacetonate, and dba (dibenzylidenacetone) complexes. The organometallic complex is not necessarily limited to that having a metal-carbon bond. The organometallic complex may be that having an organic compound at ligand moiety. Preferred examples of the organometallic complex include tetrakistriphenylphosphine palladium (Pd(PPh$_3$)$_4$) and dibenzylideneacetone palladium (Pd(dba)$_2$).

(Description on Sulfur)

For chemically modifying the gold surface with sulfur according to the present invention, a surface treatment with a solution containing a sulfur-containing acid and an oxidizer is performed, for example, by washing the surface with the solution. Examples of the sulfur-containing acid include sulfuric acid such as diluted sulfuric acid and concentrated sulfuric acid, sulfurous acid, thiosulfuric acid, polythionic acids such as trithionic acid and tetrathionic acid, and peroxydisulfuric acid. Examples of the oxidizer include hydrogen peroxide water, ozone, and oxygen plasma. The solution containing a sulfur-containing acid and an oxidizer has various combinations of the sulfur-containing acid and the oxidizer each selected from those described above. Among these variations, preferred is piranha solution. Piranha solution is a mixture of hydrogen peroxide water and concentrated sulfuric acid such as 1:3 mixture of 30% hydrogen peroxide water and concentrated sulfuric. The concentration of hydrogen peroxide water can be varied, and a mixing ratio of hydrogen peroxide water to concentrated sulfuric acid can also be varied. This means that a ratio of sulfuric acid to hydrogen peroxide, that will form Caro's acid (or persulfuric acid such as peroxysulfuric acid) H$_2$SO$_5$ and water, can be varied within the range that Caro's acid or persulfuric acid can be formed. A mechanism of providing sulfur on the gold surface is unknown, but would appear to involve a process taking advantage of strong oxidization of Caro's acid or the like. There are other methods for forming Caro's acid or persulfuric acid, including mixing sulfuric acid with ozone (SOM) (see, Patent Document 4) and oxidizing sulfuric acid with oxygen plasma (see, Patent Document 5), for example. It is also possible to electrochemically oxidize (electrolyze) sulfuric acid without an oxidizer such as hydrogen peroxide to form persulfuric acid (peroxysulfuric acid+peroxydisulfuric acid) (see, Patent Documents 6 and 7). The surface treatment with the solution containing a sulfur-containing acid and an oxidizer or the solution prepared by electrochemically oxidizing a sulfur-containing acid enables to modify the gold surface with sulfur in high grade state. It would appear that during the treatment, the sulfur-containing acid is chemically oxidized with the oxidizer or electrochemically to form Caro's acid or persulfuric acid, that Caro's acid or persulfuric acid activates the gold surface and simultaneously modify the gold surface with sulfur. After sulfur fixed, the surface of mesh is preferably washed with water, an organic solvent, or the like to remove remaining sulfur atoms on the mesh. Specific operations for modifying the gold surface with sulfur will be described in Examples.

The solution containing Caro's acid can also be prepared by mixing a persulfate with sulfuric acid, and optionally adjusting a concentration of the solution with water. Since mixing with water is exothermic, ice may be used together with or instead of water to adjust the concentration of solution. Examples of the persulfate include ammonium persulfate and sodium persulfate. The solution containing Caro's acid is preferably prepared under conditions of not more than 15° C. of a solution temperature with ice-cooling. Use of the mixed solution of a persulfate with sulfuric acid, similar to use of piranha solution, enables to clean the surface of the gold support and simultaneously modify the surface with sulfur in high grade state.

(Method for Fixing the Catalytic Metal Compound)

The catalytic metal compound can be fixed by any method. The method generally comprises contacting a solution or suspension of the catalytic metal compound in an organic solvent with a solid support having the gold surface modified with sulfur. The catalytic metal compound can be bonded or adsorbed on the solid support having the gold surface modified with sulfur through contact with the solid support. Contacting may be performed with heating if needed. In fixing, the catalytic metal compound may be contacted with the solid support alone or in the presence of an additive according to need. The additive is preferably triphenylphosphine. The heating temperature is not specifically limited. The temperature is generally set up to the boiling point of the organic solvent used. Preferred examples of the organic solvent include nitriles such as acetonitrile and aromatic compounds such as toluene and xylene. In fixing, the organic solvent can be used as is, but preferably after degassed with an inert gas such as argon. The time of fixing the catalytic metal compound is preferably 5 to 20 hours, and more preferably 10 to 20 hours in the organic solvent with heating. The concentration of the catalytic metal compound is not specifically limited. The concentration is generally 0.001% by mole to 10% by mole, and preferably 0.01% by mole to 5% by mole base on a concentration of metal elements.

After the catalytic metal compound bonded, the mesh is washed with an organic solvent described below to remove remaining metals on the mesh. A process of washing the mesh is performed after the catalytic metal compound is fixed, and comprises immersing the mesh bonded with the catalytic metal compound in an organic solvent and heating the solvent. The organic solvent is preferably those having a boiling point of 50° C. to 250° C., and preferably 50° C. to 200° C. and no reactive functional group. Preferred examples of the solvent include nitriles such as acetonitrile and benzonitrile and aromatic hydrocarbons such as toluene and xylene. The organic solvent is generally heated to a refluxing temperature of the organic solvent. The heat treatment is preferably performed under ambient pressure, or may under compressed atmosphere. The heating time is 5 to 30 hours, and preferably 10 to 20 hours.

(Catalyst Precursor)

The catalyst precursor thus produced has peaks derived from the catalytic metal compound and also sulfur as the sulfur is orbital as analyzed by photoelectron spectroscopy. In one embodiment of the present invention, the peak of the sulfur is orbital is preferably observed as a single peak. Photoelectron spectroscopy shows the peak of the sulfur is orbital around 2470 eV, more specifically within the range of 2470 eV±2 eV (not less than 2468 eV to not more than 2472 eV), and preferably within the range of 2470 eV±1 eV (not less than 2469 eV to not more than 2471 eV) in terms of the peak top position. The binding energy around 2470 eV is assigned to a peak of the is orbital of zero-, mono-, or divalent sulfur, and preferably the is orbital of zerovalent sulfur. The fact that the peak of the sulfur is orbital can be found within the range of 2470 eV±2 eV in terms of the peak top position suggests that sulfur atoms adsorbed or bonded on the gold surface are well-ordered. Particularly when the peak of the sulfur is orbital appears as a single peak, it suggests that sulfur atoms adsorbed or bonded on the gold surface are highly well-ordered. When the peak of the sulfur is orbital appears as the largest peak within the range of 2470 eV±2 eV in terms of the peak top position, other peak (peak derived from impurity or the like) preferably has an area of not more than 0.35, and more preferably not more than 0.13, based on the normalized area of the largest peak to 1. In particularly preferred cases, other peak has an area equal to 0, or there is only a single peak within the range. In the surface-treated structure, the peak of the sulfur is orbital appears around 2478 eV, or within the range of tetravalent sulfur. When the structure is bonded with the catalytic metal compound, the peak shifts to around 2470 eV, particularly within the range of 2470 eV±2 eV in terms of the peak top position, or within the range of the sulfur is orbital of zero-, mono-, or divalent sulfur, and preferably of zerovalent sulfur. In the present invention, for photoelectron spectroscopy, preferably used is Synchrotron radiation Hard X-ray Photoelectron Spectroscopy (SR-HXPS).

(Reaction Using the Catalyst Precursor)

The catalyst precursor of the present invention does not exhibit a catalytic activity by itself, but gradually releases the catalytic metal compound supported on the catalyst precursor in the immersed state in a desired reaction solution, that gradually released catalytic metal compound is a catalytically active species. For example, the method for using the catalyst precursor according to the present invention comprises preparing a solution containing a halogenated hydrocarbon compound as a raw material or apart of raw materials and immersing the catalyst precursor according to the present invention in the solution to release the catalytically active species from the catalyst precursor. The halogenated hydrocarbon compound will be exemplified in respective reactions described below.

The catalyst precursor of the present invention can be used in any organic reaction as long as, if the catalyst precursor is for example in a mesh form, the catalytic metal compound supported on the mesh is active in the reaction. The reaction is not limited to that forming a new bond as described above. The reaction includes hydrogen reduction, asymmetric synthesis, and substitution, and the like. The present invention provides the sulfur modified gold-supported metal catalyst precursor, that has a novel composition of three components "Au-sulfur-metal" in which the catalytic metal compound is directly supported on sulfur-modified Au, that has characteristic sulfur modification well-ordered on the gold surface as appearing a single peak derived from the sulfur is orbital as well as a peak derived from the catalytic metal compound as analyzed by photoelectron spectroscopy, and owing to the well-ordered modification, that can be recycled some times, preferably ten times or more with almost no departure of the catalytic metal compound in a reaction solution used. In the present invention, use of the sulfur-modified Au (including a gilded surface) as a solid support can solve the problems of the mesh by itself of the catalyst precursor in safety and stability. The catalyst precursor is also suitably processed in to a desired form such as plate and cylinder, resulting in the possibility of introduction into a reactor or the like.

(Suzuki-Miyaura Coupling)

The present invention provides the method for producing an organic compound using the sulfur modified Au-supported metal catalyst precursor of the present invention, comprising contacting a starting organic compound with the metal catalyst precursor to form a new bond between carbon and carbon or hetero atom. The method of the present invention is preferably applied to condensation of an aryl or alkenyl halide with an arylboron or vinylboron derivative using the metal catalyst precursor of the present invention containing Pd derived from a palladium compound such as $Pd(OAc)_2$ as the catalytic metal compound to produce a diaryl derivative, an alkenylaryl derivative, or a 1,3-diene compound. For example, the method of the present invention produces a biphenyl derivative by condensation of a halogenated benzene with phenylboronic acid.

Examples of the halogen of the aryl or alkenyl halide in the method of the present invention include a chlorine, bromine, and an iodine atoms. Examples of the aryl group of the aryl halide include carbocyclic and heterocyclic aromatic groups. Examples of the carbocyclic aromatic group include monocyclic, polycyclic, and condensed-cyclic carbocyclic aromatic groups having 6 to 36 carbon atoms, preferably 6 to 18 carbon atoms, and more preferably 6 to 12 carbon atoms. Specific examples of the carbocyclic aromatic group include phenyl, naphthyl, biphenyl, phenanthryl, and anthryl. Examples of the heterocyclic aromatic group include monocyclic, polycyclic, and condensed-cyclic heterocyclic groups having a 3- to 8-membered ring, and preferably 5- to 8-membered ring containing 1 to 4, preferably 1 to 3, and more preferably 1 to 2 hetero atoms selected from nitrogen, oxygen, and sulfur. Specific examples of the heterocyclic group include furyl, thienyl, pyrrolyl, pyridyl, indole, and benzoimidazolyl. These aryl groups may be substituted. Any substituent can be introduced as long as it does not adverse affect the reaction. Examples of the substituent include halogen atoms as described above, nitro groups, substituted or unsubstituted alkyl groups having 1 to 20 carbon atoms and preferably 1 to 10 carbon atoms, substituted or unsubstituted alkoxy groups having 1 to 20 carbon atoms and preferably 1 to 10 carbon atoms, and substituted or unsubstituted alkoxycarbonyl groups having 1 to 20 carbon atoms and preferably 1 to 10 carbon atoms. Examples of the alkenyl group of the alkenyl halide include substituted or unsubstituted vinyl groups. Examples of the substituent of the vinyl group include substituted or unsubstituted alkyl groups having 1 to 20 carbon atoms and preferably 1 to 10 carbon atoms, substituted or unsubstituted alkenyl groups having 1 to 20 carbon atoms and preferably 1 to 10 carbon atoms, substituted or unsubstituted aryl groups having 6 to 20 carbon atoms and preferably 6 to 10 carbon atoms, and substituted or unsubstituted aralkyl groups having 7 to 20 carbon atoms and preferably 7 to 12 carbon atoms. Any substituent can be introduced as long as it does not adverse affect the reaction.

Examples of the boron derivative in the method of the present invention include orthoboric acid mono-, di-, and triesters and derivatives thereof. The boron derivative is not necessarily limited to orthoboric acid and derivative thereof. Examples of the aryl group of the arylboron derivative include aromatic rings such as a phenyl, a naphthyl, a pyridine, and a furyl groups, which may be substituted or unsubstituted. Any substituent can be introduced as long as it does not adverse affect the reaction. Examples of the substituent include halogen atoms such as a chlorine, a bromine, and an iodine atoms, substituted or unsubstituted alkyl groups having 1 to 20 carbon atoms and preferably 1 to 10 carbon atoms, and substituted or unsubstituted alkoxy groups having 1 to 20 carbon atoms and preferably 1 to 10 carbon atoms. Examples of the vinyl group of the vinylboron derivative include substituted or unsubstituted vinyl groups. Any substituent can be introduced as long as it does not adverse affect the reaction.

The method of the present invention is preferably performed in a polar solvent such as acetonitrile and ethanol. The reaction temperature can be selected within the range from a room temperature to the boiling point of the solvent used.

Since the catalyst precursor of the present invention is in the solid phase, an intended product can be provided after the reaction by taking off the solid catalyst precursor, separating the product by standard treatments such as condensation and extraction, and purifying and isolating by various means for purification.

(Mizorogi-Heck Reaction)

The method for producing an organic compound using the sulfur modified Au-supported metal catalyst precursor of the present invention is preferably applied to condensation of an alkene with a halide or sulfonate having a carbon-carbon double bond using the palladium catalyst precursor of the present invention containing Pd derived from a palladium compound such as $Pd(OAc)_2$ as the catalytic metal compound to produce an arylalkene compound or a 1,3-diene compound.

Examples of the alkene in the method of the present invention include ethylene derivatives having at least one hydrogen atom. The ethylene derivative is more preferably substituted at least one hydrogen atom on ethylene with a keto group, a substituted or unsubstituted alkoxycarbonyl group, and/or a substituted or unsubstituted aryl group. Examples of the aryl group include carbocyclic and heterocyclic aromatic groups as described above. Any substituent can be introduced as long as it does not adverse affect the reaction. Examples of the substituent include those described above. More preferred examples of the alkene include substituted or unsubstituted 3-ketoalkenes, substituted or unsubstituted styrene derivatives, and substituted or unsubstituted (meta)acrylic acid esters. Examples of the ester residue of the (meta)acrylic acid ester include substituted or unsubstituted alkyl groups having 1 to 20 carbon atoms and preferably 1 to 10 carbon atoms.

Any substituent can be introduced as long as it does not adverse affect the reaction. Preferred examples of the alkene include, but not limited to, (meta)acrylic acid esters such as methyl acrylate, 3-ketoalkenes such as 3-ketobutene, and styrene derivatives such as styrene.

Examples of the halogen of the halide having a carbon-carbon double bond in the method of the present invention include a chlorine, a bromine, and an iodine atoms. Examples of the sulfonate having a carbon-carbon double bond include sulfonic acid and derivatives thereof, including metal salts of sulfonic acid such as sodium sulfonate or potassium sulfonate and ammonium salts. The group having a carbon-carbon double bond is only required to have a carbon-carbon double bond, and may be aliphatic or aromatic. Examples of the group include substituted or unsubstituted vinyl groups and substituted or unsubstituted aryl groups. Examples of the aryl group include carbocyclic and heterocyclic aromatic groups as described above. Any substituent can be introduced as long as it does not adverse affect the reaction.

The method of the present invention is preferably performed in a polar solvent such as acetonitrile and ethanol. The reaction temperature can be selected within the range from a room temperature to the boiling point of the solvent used.

Since the catalyst precursor of the present invention is in the solid phase, an intended product can be provided after the reaction by taking off the solid catalyst precursor, separating the product by standard treatments such as condensation and extraction, and purifying and isolating by various means for purification.

(Stille Coupling)

The method for producing an organic compound using the sulfur modified Au-supported metal catalyst precursor of the present invention is preferably applied to condensation of a tin compound having a carbon-carbon double bond with an aryl or alkenyl halide using the palladium catalyst precursor of the present invention containing Pd derived from a palladium compound such as $Pd(OAc)_2$ as the catalytic metal compound to produce a biaryl compound, an arylalkene compound or a 1,3-diene compound.

The tin compound in the method of the present invention can be substituted with an aryl groups or the like. Examples of the aryl group include aromatic rings such as phenyl, naphthyl, pyridin, and furyl groups, which may be substituted or unsubstituted. Any substituent can be introduced as long as it does not adverse affect the reaction. Examples of the substituent include halogen atoms such as a chlorine, a bromine, and an iodine atoms, substituted or unsubstituted alkyl groups having 1 to 20 carbon atoms and preferably 1 to 10 carbon atoms, and substituted or unsubstituted alkoxy groups having 1 to 20 carbon atoms and preferably 1 to 10 carbon atoms. The tin compound may also have a vinyl group which may be substituted or unsubstituted. Any substituent can be introduced as long as it does not adverse affect the reaction.

The method of the present invention is preferably performed in a polar solvent such as acetonitrile and ethanol. The reaction temperature can be selected within the range from a room temperature to the boiling point of the solvent used.

Since the catalyst precursor of the present invention is in the solid phase, an intended product can be provided after the reaction by taking off the solid catalyst precursor, separating the product by standard treatments such as condensation and extraction, and purifying and isolating by various means for purification.

(Sonogashira Coupling)

The method for producing an organic compound using the sulfur modified Au-supported metal catalyst precursor of the present invention is preferably applied to condensation of an alkyne with a halide having a carbon-carbon double bond using the palladium catalyst precursor of the present invention containing Pd derived from a palladium compound such as Pd (OAc)$_2$ as the catalytic metal compound to produce an arylalkyne or an alkynylalkyne.

Examples of the substituent of the alkyne in the method of the present invention include aromatic groups such as phenyl, naphthyl, pyridyl, and furyl groups, which may be substituted or unsubstituted. Any substituent can be introduced as long as it does not adverse affect the reaction. Examples of the substituent include halogen atoms such as a chlorine, bromine, and iodine atoms, substituted or unsubstituted alkyl groups having 1 to 20 carbon atoms and preferably 1 to 10 carbon atoms, and substituted or unsubstituted alkoxy groups having 1 to 20 carbon atoms and preferably 1 to 10 carbon atoms. The alkyne may also have a vinyl group which may be substituted or unsubstituted. Any substituent can be introduced as long as it does not adverse affect the reaction.

Examples of the halogen of the halide having a carbon-carbon double bond in the method of the present invention include chlorine, bromine, and iodine atoms. Examples of the sulfonate having a carbon-carbon double bond include sulfonic acid and derivatives thereof, including metal salts of sulfonic acid such as sodium sulfonate or potassium sulfonate and ammonium salts. The group having a carbon-carbon double bond is only required to have a carbon-carbon double bond, and may be aliphatic or aromatic. Examples of the group include substituted or unsubstituted vinyl groups and substituted or unsubstituted aryl groups. Examples of the aryl group include carbocyclic and heterocyclic aromatic groups as described above. Any substituent can be introduced as long as it does not adverse affect the reaction.

The method of the present invention is preferably performed in a polar solvent such as acetonitrile and ethanol. The reaction temperature can be selected within the range from a room temperature to the boiling point of the solvent used.

Since the catalyst precursor of the present invention is in the solid phase, an intended product can be provided after the reaction by taking off the solid catalyst precursor, separating the product by standard treatments such as condensation and extraction, and purifying and isolating by various means for purification.

(Buchwald-Hartwig Coupling)

The method for producing an organic compound using the sulfur modified Au-supported metal catalyst precursor of the present invention is preferably applied to formation of a carbon-hetero atom bond, more preferably a carbon-oxygen or a carbon-sulfur bond, and even more preferably a carbon-nitrogen bond, using the palladium catalyst precursor of the present invention containing Pd derived from a palladium compound such as Pd(OAc)$_2$ as the catalytic metal compound. For example, the method of the present invention is applied to condensation of an amine having at least one alkyl or aryl group with a halide having a carbon-carbon double bond to produce a substituted amine.

Examples of the substituent of the amine in the method of the present invention include substituted or unsubstituted alkyl groups having 1 to 20 carbon atoms and preferably 1 to 10 carbon atoms and substituted or unsubstituted aromatic groups such as phenyl, naphthyl, pyridyl, and furyl groups. Any substituent can be introduced as long as it does not adverse affect the reaction. Examples of the substituent include halogen atoms such as a chlorine, a bromine, and an iodine atoms, substituted or unsubstituted alkyl groups having 1 to 20 carbon atoms and preferably 1 to 10 carbon atoms, and substituted or unsubstituted alkoxy groups having 1 to 20 carbon atoms and preferably 1 to 10 carbon atoms.

Examples of the halogen of the halide having a carbon-carbon double bond in the method of the present invention include a chlorine, a bromine, and an iodine atoms. Examples of the sulfonate having a carbon-carbon double bond include sulfonic acid and derivatives thereof, including metal salts of sulfonic acid such as sodium sulfonate or potassium sulfonate and ammonium salts. The group having a carbon-carbon double bond is only required to have a carbon-carbon double bond, and may be aliphatic or aromatic. Examples of the group include substituted or unsubstituted vinyl groups and substituted or unsubstituted aryl groups. Examples of the aryl group include carbocyclic and heterocyclic aromatic groups as described above. Any substituent can be introduced as long as it does not adverse affect the reaction.

The method of the present invention is preferably performed in a polar solvent such as acetonitrile and ethanol. The reaction temperature can be selected within the range from a room temperature to the boiling point of the solvent used.

Since the catalyst precursor of the present invention is in the solid phase, an intended product can be provided after the reaction by taking off the solid catalyst precursor, separating the product by standard treatments such as condensation and extraction, and purifying and isolating by various means for purification.

EXAMPLES

The present invention will be described in more detail below with literature to Examples, but should not be construed as being limited thereto.

(First Stage: Characteristics of the Structure of the Catalyst Precursor According to the Present Invention at the Atom/Molecular Level)

(Property of Sulfur Modification on the Au Surface)

Arisawa, one of the present inventors, reported in Patent Document 2 that he developed a "metal catalyst prepared by bonding or adsorbing molecules or atoms on the surface of a material and further bonding or adsorbing an organometallic complex on the molecules or atoms". However, actually developed in that stage was only a "metal catalyst prepared by adsorbing sulfur on the surface of a gallium arsenide (001) substrate through a treatment with ammonium polysulfide and adsorbing a palladium catalyst thereon" as described in Example of the patent. Although the patent describes various possible materials and metal complexes, suitable materials and metal complexes could not be easily imagined by analogy. The patent also describes various possible molecules or atoms linking the material and the metal complex. However, actually usable in that stage was only sulfur. The patent also could not find a practical way of fixing sulfur other than the treatment with ammonium polysulfide. The greatest disadvantage of the "metal catalyst prepared by adsorbing sulfur on the surface of a gallium arsenide (001) substrate through a treatment with ammonium polysulfide and adsorbing a palladium catalyst thereon" was leakage of gallium and/or arsenic into a reaction system through corrosion of the gallium arsenide (001) substrate in use of the catalyst. In order to develop a new catalyst without gallium or arsenic and a truly environment-conscious catalyst, the present inventors have surveyed various substances for the material, but failed to develop a catalyst superior to the "metal catalyst prepared by adsorbing sulfur on the surface of a gallium arsenide (001) substrate through a treatment with ammonium polysulfide and adsorbing a palladium catalyst thereon." For example, a "metal catalyst prepared by adsorbing sulfur on the surface of a gold (111) substrate through a treatment with ammonium polysulfide and adsorbing a palladium catalyst thereon"

according to Patent Document 2 under conditions and items known within the range of the description was a substance covered with a black film on the surface and difficult to be analyzed by photoelectron spectroscopy. In addition, the catalyst exhibited insufficient activities (for example, in the Suzuki-Miyaura coupling, see Formula 1 and Table 1).

[Formula 1]

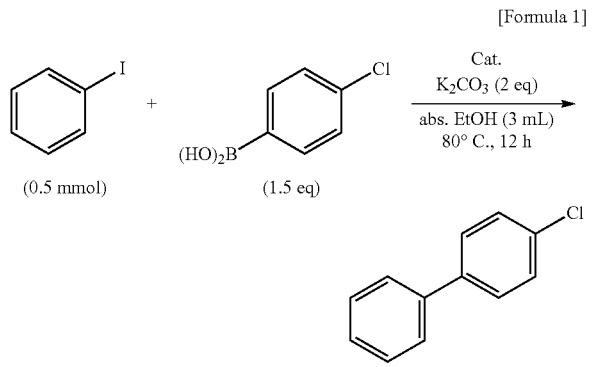

TABLE 1

| | NUMBER OF REACTION | | | | | | | | | |
|---|---|---|---|---|---|---|---|---|---|---|
| | 1st | 2nd | 3rd | 4th | 5th | 6th | 7th | 8th | 9th | 10th |
| YIELD (%) | 99 | 79 | 65 | 68 | 3 | — | — | — | — | — |

In a series of study for developing a solid-supported catalysts, the present inventors were driven by necessity to make a "metal catalyst prepared by directly fixing a palladium complex on a gold (111) substrate" as a control sample. Direct modification of a gold (111) substrate is generally performed by cleaning the surface of the substrate with piranha solution (30% hydrogen peroxide solution:concentrated sulfuric acid=1:3). Thus, the present inventors made a "metal catalyst precursor prepared by treating a gold (111) substrate with piranha solution and adsorbing a palladium complex thereon." The catalyst precursor was a glossy substance having the same gold color to that of the gold substrate. This exhibited high activity (Table 2) in the Suzuki-Miyaura coupling (see, Formula 1) and could be recycled.

TABLE 2

| | NUMBER OF REACTION | | | | | | | | | |
|---|---|---|---|---|---|---|---|---|---|---|
| | 1st | 2nd | 3rd | 4th | 5th | 6th | 7th | 8th | 9th | 10th |
| YIELD (%) | 96 | 95 | 97 | 96 | 98 | 99 | 99 | 96 | 96 | 99 |

Analysis of the catalyst precursor by photoelectron spectroscopy surprisingly revealed respective presence of sulfur and palladium on the substrate (at 2470 eV for the sulfur is orbital and at 3174 eV for the palladium 2p orbital). At first, an origin of sulfur could not be determined, because of the process of production. Further analysis by photoelectron spectroscopy was performed, and more surprisingly, it was newly found that the treatment with piranha solution for cleaning the surface functioned as fixing sulfur on the gold (111) substrate (at 2478 eV for the sulfur is orbital). In other words, the catalyst produced as a "metal catalyst prepared by treating a gold (111) substrate with piranha solution and adsorbing a palladium complex thereon" was found to be a "metal catalyst precursor prepared by adsorbing sulfur on the surface of the gold (111) substrate by the treatment with piranha solution and adsorbing the palladium complex." As described above, the catalyst precursor cannot be produced through the conventional method for fixing sulfur by the treatment with ammonium polysulfide. The catalyst precursor contains no gallium or arsenic having concerns about health, has high durability, and is desired to be developed the practical use.

Comparative Example 1

Preparation of a "Metal Catalyst Obtained by Adsorbing Sulfur on the Surface of a Gold (111) Substrate by a Treatment with Ammonium Polysulfide and Further Adsorbing a Palladium Complex Thereon"

A gold (111) substrate (10 mm by 11 mm, annealed on Mica) was immersed in an ammonium polysulfide solution (S content: 5 to 7%, 3.0 mL) for 30 minutes at 60° C. and washed with water and acetonitrile. Then, the resultant substrate was vacuum-dried for 10 minutes under a reduced pressure of 6 mmHg at a room temperature, and dried for additional 20 minutes with heating with a heat gun to give a gold (111) substrate on which sulfur (S) was bonded or adsorbed. Next, the resultant gold (111) substrate (S—Au) bonded or adsorbed to sulfur was stirred in a acetonitrile solution (3.0 mL) containing tetrakistriphenylphosphine palladium (Pd(PPh$_3$)$_4$) (25 mg) as the organometallic complex for 12 hours to bond or adsorb palladium (Pd) (0.2 to 0.4 mg), thereby preparing a metal catalyst according to Patent Document 2 under conditions and items known within the range of the description. The resultant substrate was immersed in a washing liquid composed of acetonitrile for cleaning until the substrate became catalytically deactive. The resultant metal catalyst was covered with a black film on the surface and hard to be analyzed by photoelectron spectroscopy. In addition, the metal catalyst had insufficient activities (for example, in Suzuki-Miyaura coupling (formula 1)).

Example 1

Preparation of a "Metal Catalyst Precursor Obtained by Treating the Surface of a Gold (111) Substrate with Piranha Solution and Adsorbing a Palladium Complex Thereon"

A gold (111) substrate (10 mm by 11 mm, annealed on Mica) was immersed in a mixed solution (piranha solution) of 35% hydrogen peroxide water (1.0 mL) and concentrated sulfuric acid (3.0 mL) for 3 minutes, washed with water and ethanol, and dried under reduced pressure to obtain a gold (111) substrate on which sulfur (S) was bonded or adsorbed (2478 eV for the sulfur is orbital). The resultant gold (111) substrate bonded or adsorbed to sulfur was stirred in a xylene solution (3.0 mL) containing bis(benzylideneacetate) palladium (Pd(dba)$_2$) (13.6 mg) for 12 hours at 100° C. to bond or adsorb palladium (Pd) (0.2 to 0.4 mg). The resultant substrate was washed with a washing liquid composed of xylene and dried under a reduced pressure of 6 mmHg at room temperature to obtain a crude metal catalyst precursor comprising the gold (111) substrate on which sulfur (S) was bonded or adsorbed and Pd further bonded or adsorbed thereon. The crude metal catalyst precursor was heated in a solution composed of xylene for 12 hours at 135° C., sufficiently washed with a solution composed of xylene, and vacuum-dried for 10 minutes under a reduced pressure of 6 mmHg to obtain a metal catalyst precursor according to the present invention. The catalyst precursor was a glossy substance having the same gold color to that of the original gold substrate. The catalyst precursor exhibited high activity in the Suzuki-Miyaura coupling (FIG. 2) and could be recycled. Analysis of the catalyst precursor by photoelectron spectroscopy surprisingly revealed respective presence of sulfur and palladium on the substrate (at 2470 eV for the sulfur is orbital and at 3174 eV for the palladium 2p orbital). For photoelectron spectroscopy, used was Synchrotron radiation Hard X-ray Photoelectron Spectroscopy (SR-HXPS). Hard X-ray Photoelectron Spectroscopy was performed with Synchrotron radiation in BL15XU at SPring-8. Core-level and valence-band spectra by photoelectron spectroscopy were observed with high energy X-ray radiation of hv=5945 eV. An energy resolution was estimated to be 0.26 eV from the Fermi edge of gold (Au). A bond energy was normalized (calibrated) with a photoelectron intensity of the Au $4f_{7/2}$ (84.0 eV). Each sample was attached to a copper sample holder with a conductive adhesive tape. The conductive adhesive tape served for shorting a distance between the surface of the sample and the sample holder to prevent the sample from charging.

(Second Stage: Study for Use of the Catalyst Precursor According to the Present Invention)

Preparation of Au—S

Example 2

A 100-mesh net of fine gold (12 mm by 14 mm, wire diameter of 0.1 mm, opening of 0.154 mm) was immersed in a mixed solution (piranha solution) of 35% hydrogen peroxide water (1 mL) and concentrated sulfuric acid (3 mL) for 3 minutes, taken off, washed with water and further ethanol, and dried under reduced pressure to obtain a sulfur-modified Au.

Preparation 1 of Au—S—Pd

Example 3

The sulfur-modified Au prepared in Example 2 was added to a xylene solution (3 mL) containing Pd (OAc)$_2$ (5.3 mg) to be stirred for 12 hours at 100° C. The resultant crude mesh catalyst precursor was washed with xylene and dried under reduced pressure. The dried crude mesh catalyst precursor was added to xylene (3 mL) to be stirred for 12 hours at 135° C. Then, washed with xylene and dried under reduced pressure, a mesh catalyst precursor having 87 μg of sulfur and 38 μg of Pd on the surface of substrate was obtained.

Preparation 2 of Au—S—Pd

Example 4

The sulfur-modified Au prepared in Example 2 was stirred in a solution of Pd(dba)$_2$ (13.8 mg) in xylene (3 mL) for 12 hours at 100° C. The resultant crude mesh catalyst precursor was washed with xylene and dried under reduced pressure. The dried crude precursor was heated in xylene (3 mL) for 12 hours at 135° C. The heated precursor was washed with xylene and dried under reduced pressure to give a mesh catalyst precursor having 80 μg of Pd on the surface of substrate.

Standard Suzuki-Miyaura Coupling

Example 5

To a solution of iodobenzene (102 mg), 4-chlorophenylboronic acid (117 mg), and potassium carbonate (138 mg) in ethanol (3 ml) was added the mesh catalyst precursor (12 mm by 14 mm) prepared in Example 3 and heated for 12 hours at 80° C. The reaction mixture was cooled to room temperature, and the mesh catalyst precursor was washed with ethanol and taken off from the mixture. The solvent was distilled away from the reaction mixture under reduced pressure. The residue was purified by column chromatography on silica gel (n-hexane) to give an intended product, 4-chlorobiphenyl quantitatively. The mesh catalyst precursor taken off from the mixture was again used in the same reaction to again give the intended product, 4-chlorobiphenyl quantitatively. The mesh catalyst precursor could be recycled at least thirty times.

Preparation of a Catalyst Using Au-Plating (by a Dry or Wet Method)

Example 6

A 100-mesh net of copper wire (12 mm by 14 mm, a wire diameter of 0.1 mm, opening of 0.154 mm) subjected to gold plating by a wet process was treated in the same procedures as in Example 2 followed by Example 3 to give a mesh catalyst precursor in which Pd is supported on the surface of the substrate (wet-gilded type). A mesh catalyst precursor (dry-gilded type) was prepared from the same net by gilding by a dry method and treated in the same way.

Suzuki-Miyaura Coupling Using a Plated Mesh Catalyst Precursor with a Gilded Mesh Example 7

To a solution of iodobenzene (102 mg), 4-chlorophenylboronic acid (117 mg), and potassium carbonate (138 mg) in ethanol (3 ml) was added the plated mesh catalyst precursor (12 mm by 14 mm, wire diameter of 0.1 mm, opening of 0.154 mm) prepared in Example 6 and heated for 12 hours at 80° C. The reaction mixture was cooled to room temperature, and the mesh catalyst precursor was taken off from the mixture and washed with ethanol. The solvent was distilled away from the reaction mixture under reduced pressure. The residue was purified by column chromatography on silica gel (n-hexane) to give an intended product, 4-chlorobiphenyl quantitatively. The catalyst precursor taken off from the mixture could be recycled at least ten times with an average yield of not less than 90%. The wet-gilded type and the dry-gilded type provided the similar results.

Mesh Catalyst Precursor Sterically-Combined with Each Other to Form a Three-dimensional Structure Example 8

Three mesh catalyst precursors (12 mm by 14 mm, wire diameter of 0.1 mm, opening of 0.154 mm) prepared in Example 4 were wrapped around a stirring bar of a cross shape to give a sterically-combined catalytic stirring bar. To an ethanol solution (3 ml) containing bromobenzene (77.1 mg), 4-chlorophenylboronic acid (117 mg), and potassium carbonate (138 mg) the catalytic stirring bar was added to be gently stirred and concurrently heated to 80° C. for 12 hours. The reaction mixture was cooled to room temperature and a part of the reaction mixture was taken for calculating a yield. HPLC analysis showed that a yield of an intended product, 4-chlorobiphenyl was 28%.

Preparation of Catalyst with Ru

Example 9

To a xylene solution (3 ml) containing $Ru(C_{12}H_{18})Cl_2$ (4.1 mg) the sulfur-modified Au prepared in Example 2 was added to be stirred for 12 hours at 100° C. The resultant crude mesh catalyst precursor was washed with xylene and dried under reduced pressure. The dried crude mesh catalyst precursor was added to a xylene solution (3 mL) to be heated for 12 hours at 135° C. Then, washed with xylene and dried under reduced pressure, a mesh catalyst precursor having Ru on the surface of substrate was obtained.

Example Using a Catalyst Having Ru for a Reaction)

Example 10

To an ethanol solution (3 ml) containing 4-iodobenzene (102 mg), 4-chlorophenylboronic acid (117 mg), and potassium carbonate (138 mg) the mesh catalyst precursor (12 mm by 14 mm, wire diameter of 0.1 mm, opening of 0.154 mm) prepared in Example 9 was added to be heated for 12 hours at 80° C. The reaction mixture was cooled to room temperature and apart of the reaction mixture was taken for calculating an yield. HPLC analysis showed that a yield of an intended product, 4-chlorobiphenyl was 57%.

Mizorogi-Heck Reaction

Example 11

To a acetonitrile solution (3 ml) containing iodobenzene (102 mg), methylester acrylate (64.6 mg), and triethylamine (101 mg) the mesh catalyst precursor (12 mm by 14 mm, wire diameter of 0.1 mm, opening of 0.154 mm) prepared in Example 3 was added to be heated for 12 hours at 100° C. Then, an intended product, trans-methyl cinnamate quantitatively was obtained. The used mesh catalyst precursor was again used in the same reaction to again give the intended product, trans-methyl cinnamate quantitatively. The mesh catalyst precursor could be recycled at least ten times.

Stille Coupling

Example 12

To an ethanol solution (3 ml) containing 4-nitroiodobenzene (125 mg), tributylvinyltin (174 mg), and potassium carbonate (138 mg) the mesh catalyst precursor (12 mm by 14 mm, wire diameter of 0.1 mm, opening of 0.154 mm) prepared in Example 3 was added to be heated for 12 hours at 80° C. The reaction mixture was cooled to room temperature, and the mesh catalyst precursor was washed with ethanol to be taken off from the reaction mixture. The solvent was distilled from the reaction mixture under reduced pressure. The residue was purified by column chromatography on silica gel (n-hexane:ethyl acetate=4:1) to give an intended product, 4-nitrostyrene with 90% yield. The mesh catalyst precursor taken off from the mixture was again used in the same reaction to again give the intended product, 4-nitrostyrene with 88% yield. The mesh catalyst precursor could be recycled at least ten times.

Sonogashira Coupling

Example 13

To an ethanol solution (3 ml) containing iodobenzene (102 mg), phenylacetylene (56.1 mg), and potassium carbonate (138 mg) the mesh catalyst precursor (12 mm by 14 mm, wire diameter of 0.1 mm, opening of 0.154 mm) prepared in Example 3 was added to be heated for 12 hours at 80° C. The reaction mixture was cooled to room temperature, and the mesh catalyst precursor was washed with ethanol to be taken off from the mixture. The solvent was distilled away from the reaction mixture under reduced pressure. The residue was purified by column chromatography on silica gel (n-hexane) to give an intended product, diphenylacetylene with 15% yield.

Buchwald-Hartwig Coupling

Example 14a

To a toluene solution (3 ml) containing iodobenzene (102 mg), 1,4-dioxa-8-azaspiro[4.5]decane (85.9 mg), and tert-butoxysodium (67.3 mg) the mesh catalyst precursor (12 mm by 14 mm, wire diameter of 0.1 mm, opening of 0.154 mm) prepared in Example 3 was added to be heated for 24 hours at 100° C. The reaction mixture was cooled to room temperature, and the mesh catalyst precursor was taken off from the mixture and washed with ethanol. The solvent was distilled away from the reaction mixture under reduced pressure. The residue was purified by column chromatography on silica gel (n-hexane:ethyl acetate=4:1) to give an intended product, 8-phenyl-1,4-dioxia-8-azaspiro[4.5]decane with 8% yield. The mesh catalyst precursor taken off from the mixture was again used in the same reaction to again give the intended product, 8-phenyl-1,4-dioxia-8-azaspiro[4.5]decane with 12% yield.

Buchwald-Hartwig Coupling

Example 14b

To a toluene solution (3 ml) containing iodobenzene (110 mg), morpholine (73.2 mg), and tert-butoxypotassium (110 mg) the mesh catalyst precursor (12 mm by 14 mm, wire diameter of 0.1 mm, opening of 0.154 mm) prepared in Example 3 was added to be heated for 24 hours at 100° C. The reaction mixture was cooled to room temperature, and the mesh catalyst precursor was washed with ethanol to be taken off from the mixture. The solvent was distilled away from the reaction mixture under reduced pressure. The residue was purified by column chromatography on silica gel (n-hexane:ethyl acetate=9:1) to give an intended product, 4-phenylmorpholine with 62% yield. The mesh catalyst precursor taken off from the mixture was recycled in the same reaction to give the intended product, 4-phenyl-morpholine with respective yields of 61%, 57%, 58%, 54%, 58%, 58%, 53%, 53%, 53% from the second to the tenth reaction.

Polymer Synthesis

Example 15

To an ethanol solution (3 ml) of p-diiodobenzene (165 mg), 1,4-phenylenediboronic acid (124 mg), and potassium carbonate (138 mg) the mesh catalyst precursor (12 mm by 14 mm, wire diameter of 0.1 mm, opening of 0.154 mm) prepared in Example 3 was added to be heated for 12 hours at 80° C. The reaction mixture was cooled to room temperature, and the mesh catalyst precursor was washed with ethanol to be taken off from the mixture. The reaction mixture was analyzed for molecular weight of a product with a mass spectorometer to show the presence of a product having a molecular weight of not less than 1000 in the mixture.

Example 16

First, the sulfur modified gold-supported catalyst precursor of the above Example (in a mesh form) was compared with a gallium arsenide-supported catalyst (Comparative Example 2) about the amount of Pd leaked. Comparative Example 2 is the "metal catalyst prepared by adsorbing sulfur on a gallium arsenide (001) substrate by the treatment with ammonium polysulfide and adsorbing a palladium complex" prepared according to the method in Patent Document 3. Table 3 shows amounts of Pd leaked in a reaction mixture in the Suzuki-Miyaura coupling of iodobenzene (1a) and 4-chlorophenylboronic acid (2a) shown in (Formula 2) for comparing between Pd@(S)n—Au and Pd@(S)—GaAs (001). FIG. 1 is a graph showing these results. In the context, "@" is a symbol of adsorption.

[Formula 2]

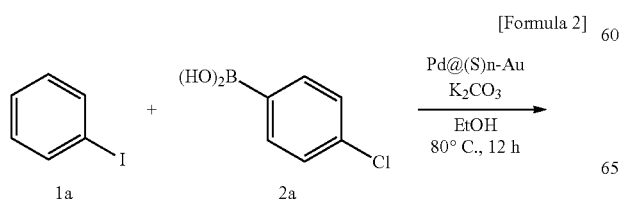

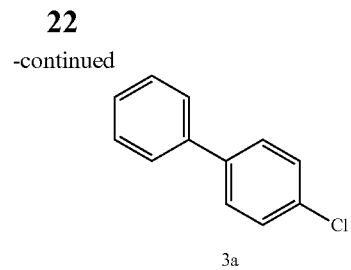

TABLE 3

Amount of released Pd into reaction mixture in Suzuki-Miyaura coupling of 1a and 2a

| Entry | Catalyst | | 1st | 2nd | 3rd | 4th | 5th | 6th | 7th | 8th | 9th | 10th | Total |
|---|---|---|---|---|---|---|---|---|---|---|---|---|---|
| 1 | Pd@(S)n-Au | (ng) | 17 | 18 | 11 | 13 | 4.0 | 10 | 7.0 | 21 | 12 | 4.0 | 117 |
| | | (ppb) | 5.7 | 5.9 | 3.9 | 4.5 | 1.3 | 3.3 | 2.4 | 7.1 | 4.1 | 1.3 | — |
| 2 | Pd@(S)n-GaAs(001) | (ng) | 340 | 710 | 640 | 830 | 690 | 380 | 330 | 580 | 240 | 120 | 4860 |
| | | (ppb) | 110 | 230 | 230 | 280 | 240 | 130 | 120 | 190 | 80 | 40 | — |

Next, these catalysts were compared about the yield when recycled. Table 4 shows yields in the Suzuki-Miyaura coupling of β-trans-iodostyrene (1b) and phenylboronic acid (2b) shown in "Formula 3" for comparing between Pd@(S)n—Au and Pd@(S)n—GaAs (001).

[Formula 3]

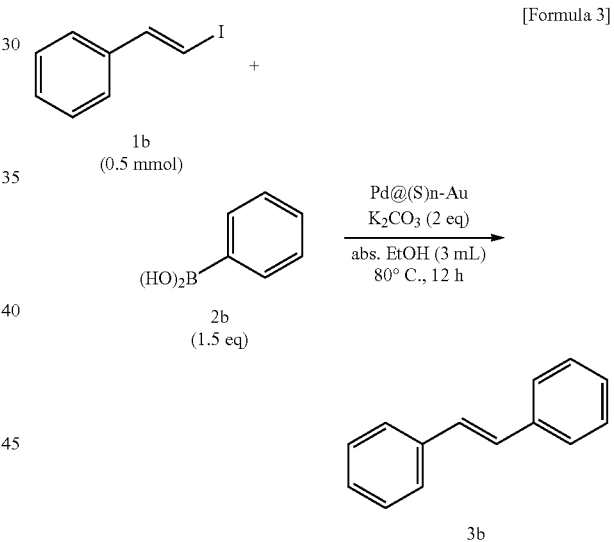

TABLE 4

| | Yield of 3b/% | | | | | | | | | |
|---|---|---|---|---|---|---|---|---|---|---|
| | 1st | 2nd | 3rd | 4th | 5th | 6th | 7th | 8th | 9th | 10th |
| Pd@(S)n-Au | 98 | 95 | 96 | >99 | 97 | 94 | 95 | 96 | 97 | 93 |
| Pd@(S)n-GaAs(001) | 95 | 78 | 88 | 71 | 91 | 87 | 84 | 54 | 26 | 22 |

Comparison between the sulfur modified gold-supported catalyst precursor of the above Example (in a mesh form) and the gallium arsenide-supported catalyst (Comparative Example 2) from the points of amount of Pd leaked and yield when recycled (Table 3, FIG. 1, and Table 4) showed the superiority of the catalyst precursor of the above Example.

(Third Stage: Study for Mechanism of Catalytically Activation of the Catalyst Precursor According to the Present Invention)

To determine which Pd is an active species in a reaction using the sulfur modified gold-supported catalyst precursor (in a mesh form), Pd released in the reaction mixture or Pd supported on (S)n—Au, two heterogeneous tests were performed.

(Three-Phase Test)

The Three-Phase test is a test using a starting material on a solid material (see, for example Non-Patent Documents 4 to 8). If an active species of a solid-supported catalyst is the solid-supported catalyst itself, then the starting material will not provide a product (the principal of no reaction between solid materials), while the active species is present in a solution (i.e., the solid-supported catalyst is a catalyst precursor), then a part of the starting material is converted to a product.

Using the sulfur modified gold-supported catalyst precursor of the above Example (in a mesh form), a reaction of an insoluble iodobenzene 4 immobilized in a resin with boronic acid 2c shown in (Formula 4) was performed in the presence or absence of soluble iodobenzene (1a). Results are shown in Table 5.

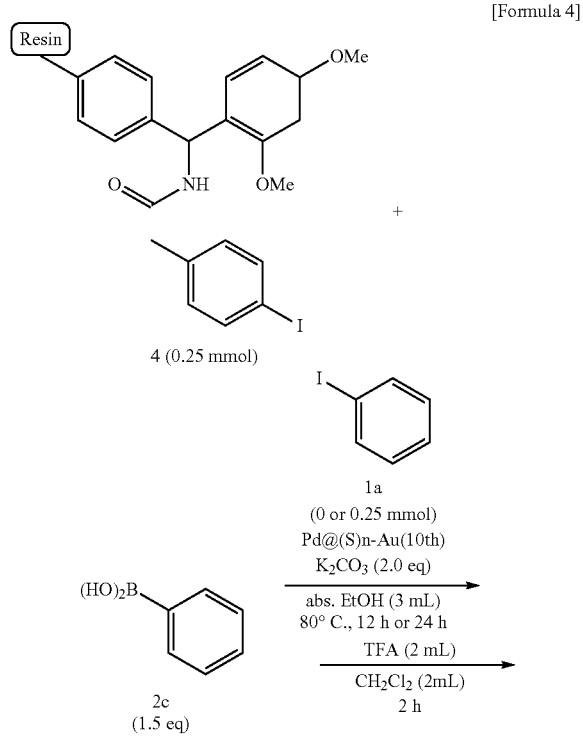

[Formula 4]

TABLE 5

| Entry | | PhI (mmol) | Reaction time (h) | Yield (%) 5 | 6 | |
|---|---|---|---|---|---|---|
| 1 | Pd@(S)n-Au | — | 12 | 78 | 0 | (9-51) |
| 2 | Pd@(S)n-Au | 0.25 | 12 | 54 | 6 | (9-26) |
| 3 | Pd@(S)n-Au | 0.25 | 24 | 43 | 32 | (9-20) |
| 4 | Pd@(S)n-GaAs(001) | 0.25 | 12 | 57 | 37 | |

In Entries 2, 3, and 4, biphenyl was produced with respective yields of 87%, 85%, and 75%.

Figure 2:
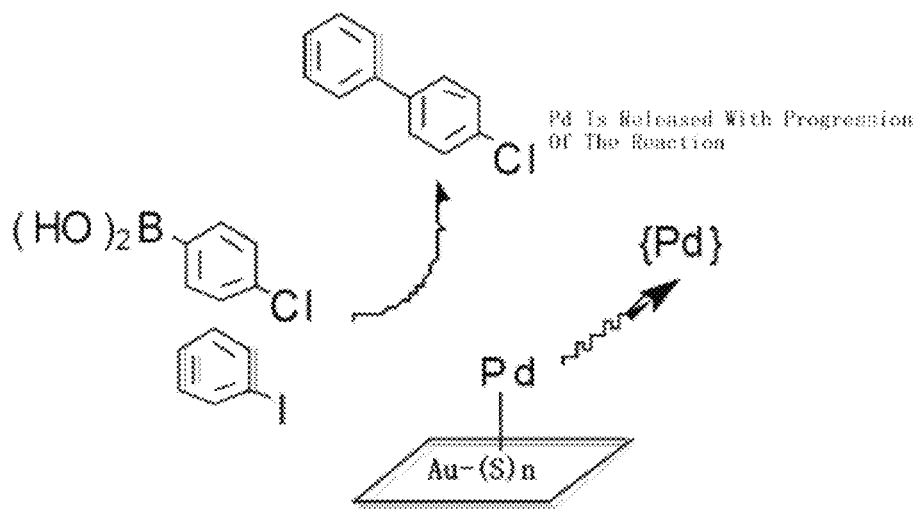
FIG. 2 is a schematic diagram showing that the sulfur modified gold-supported catalyst precursor according to the Example described below releases a very small amount of Pd into a reaction mixture when the reaction mixture contains a substance reactive to the catalytic metal compound (Pd) on (S)n—Au.

In the absence of soluble 1a, 6 resulting from the progress of the Suzuki-Miyaura coupling of insoluble 4 was not collected, but only 5 was collected. In the presence of 1a, contrary to this result, the reaction performed for 12 hours or 24 hours produced 6 resulting from the coupling of 4 with 6% or 32% yield. These results suggested that Pd catalyzing the reaction was that released from the surface of the catalyst in the reaction mixture, as shown in FIG. 2. These results also suggested that Pd on the catalyst precursor of the above Example was not released in a reaction mixture only by heating, but released in a very small amount when a reactive substance with Pd on (S)n—Au such as iodobenzene was present in the reaction mixture.

In the case of Pd@ (S)n—GaAs (001), the reaction for 12 hours produced the coupled product 6 with 37% yield. The yield of 6 reached to the similar lever for the shorter reaction time than that of the catalyst precursor of the above Example. The reason is assumed that the catalyst precursor of the above Example releases Pd in a reaction mixture in a smaller amount than that from Pd@ (S)n—GaAs (001). The results suggest that Pd binds more firmly to S on the catalyst precursor of the above Example than Pd@ (S)n—GaAs (001).

To confirm the reliability of the Three-Phase test, the sulfur modified gold-supported catalyst precursor of the above Example (in a mesh form) was also tested for a reactivity (Suzuki-Miyaura coupling) to a substrate having an amide. If the catalyst precursor of the above Example exhibits the similar reactivity to the substrate having an amide as the conventional substrate, then the Three-Phase test is reliable. Thus a model compound 7 for the supported compound 4 shown in (Formula 5) was used to examine reactivities of the catalyst precursors of Examples 10th and 11th (in a mesh form). Both catalyst precursors resulted in efficient progress of the reaction for 12 hours. These results shows that the catalyst precursor of the above Example also released a soluble catalytically active species for the substrate having an amide to show a catalytic activity, and guaranteed the reliability of the Three-Phase test system.

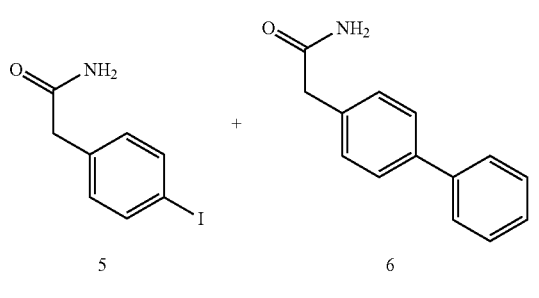

[Formula 5]

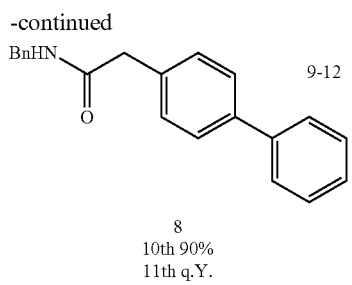

8
10th 90%
11th q.Y.

(Cold Test)

The cold test monitors an increase of a product after removal of a solid-supported catalyst from the reaction system at the certain point from the reaction start. In the case that an active species is the solid-supported catalyst itself, the product does not increase, while in the case that an active species is present in a reaction mixture (i.e., the solid-supported catalyst is a catalyst precursor), the product increases. To reveal a catalytically active species, a cold test was performed with iodoanisole (1c) and 4-chlorophenylboronic acid (2a) shown in "Formula 6"

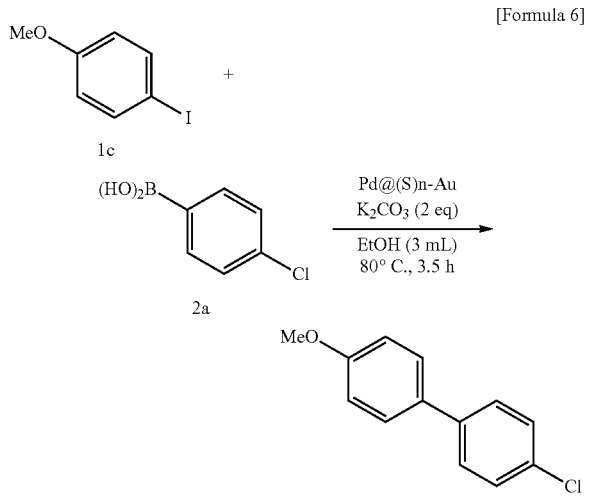

The cold test comprised cooling a reaction mixture to a room temperature at the point of 90 minutes or 30 minutes from the start of the reaction, removing the catalyst, again allowing to react, and monitoring the change overtime. Results are shown in FIG. 3. In the case of removal at the point of 90 minutes, a reaction rate decreased later in the reaction, while in the case of removal of the catalyst at the point of 30 minutes, the reaction scarcely progressed. Combining these results with the result of the Three-Phase test, the catalytically active species is assumed as Pd released from (S)n—Au into a reaction mixture. It was also found that the release of Pd in a solution requires a certain amount of time to reach a sufficient level for achieving the highest performance of the catalyst. The results also suggest that Pd is bonded to (S)n—Au at a certain strength.

These results of heterogeneous tests revealed the catalytically active species of the sulfur modified gold-supported catalyst precursor of the above Example to be a very small amount of Pd released from the catalyst precursor.

Method for Preparing a "Metal Catalyst Precursor by Treating a Gold Mesh with a Mixed Solution of a Persulfate and Sulfuric Acid and Adsorbing a Palladium Complex Thereon"

It was confirmed to be possible that a metal catalyst precursor was produced in the same way using a mixed solution of a persulfate and sulfuric acid instead of piranha solution as in Example 1.

Example 17

A solution was prepared by adding ammonium persulfate (0.63 mg) to concentrated sulfuric acid (3 ml) and stirring for 2 hours. A 100-mesh net of fine gold (12 mm by 14 mm, wire diameter of 0.1 mm, opening of 0.154 mm) was immersed in the solution for 3 minutes, washed with water and ethanol, and dried under reduced pressure to give a sulfur modified Au substrate. The resultant sulfur modified Au substrate was stirred in a solution of Pd(OAc)$_2$ (5.3 mg) in xylene (3.0 mL) for 12 hours at 100° C. to bond or adsorb palladium (Pd). The resultant substrate (mesh) was washed with a washing liquid composed of xylene and dried under a reduced pressure of 6 mmHg at a room temperature to give a crude metal catalyst precursor comprising the Au (mesh) substrate on which sulfur (S) was bonded or adsorbed and Pd further bonded or adsorbed thereon. The crude metal catalyst precursor was heated in xylene for 12 hours at 135° C., sufficiently washed with xylene, and vacuum-dried for 10 minutes under a reduced pressure of 6 mmHg to give a metal catalyst precursor according to the present invention. The catalyst precursor exhibited high activity in the Suzuki-Miyaura coupling and could be recycled.

Example 18

To concentrated sulfuric acid (4.7 g) were added sodium persulfate (4.0 g), and then ice (13 g) and water (4 g). In this operation, it is important to maintain a temperature to or below 15° C. A 100-mesh net of fine gold (12 mm by 14 mm, wire diameter of 0.1 mm, opening of 0.154 mm) was immersed in the solution for 5 minutes, washed with water and ethanol, and dried under reduced pressure to give a sulfur modified Au substrate. The resultant sulfur modified Au substrate was stirred in a solution of Pd(OAc)$_2$ (5.3 mg) in xylene (3.0 mL) for 12 hours at 100° C. to bond or adsorb palladium (Pd). The resultant substrate (mesh) was washed with a washing liquid composed of xylene and dried under a reduced pressure of 6 mmHg at a room temperature to give a crude metal catalyst precursor comprising palladium (Pd) bonded or adsorbed. The crude metal catalyst precursor was heated in xylene for 12 hours at 135° C., sufficiently washed with xylene, and vacuum-dried for 10 minutes under a reduced pressure of 6 mmHg to give a metal catalyst precursor according to the present invention. The catalyst precursor exhibited high activity in the Suzuki-Miyaura coupling and could be recycled.

INDUSTRIAL APPLICABILITY

The catalyst precursor according to the present invention enables to readily construct a new bond between carbon and carbon or hetero atom and thus can be widely used in various chemical fields including drug discovery and organic synthesis. The catalyst precursor also has good processability and can be introduced into various reaction devices and apparatuses.

The invention claimed is:

1. A catalyst precursor comprising a structure wherein the entire structure is composed of gold or a gold-based alloy and the surface of the structure is modified with elemental sulfur or at least the surface of the structure is composed of gold or a gold-based alloy and the surface of the structure is modified with elemental sulfur, and a catalytic metal compound supported on the structure, wherein the catalyst precursor has peaks derived from the catalytic metal compound and also sulfur as analyzed by photoelectron spectroscopy, and wherein the peak derived from sulfur is of the sulfur is orbital observed within a range of 2470 eV±2 eV in terms of the peak top position.

2. The catalyst precursor according to claim 1, wherein the peak of the sulfur is orbital is observed as a single peak.

3. The catalyst precursor according to claim 1, wherein the catalytic metal compound is a metal salt or metal complex containing at least one of ruthenium, rhodium, iridium, palladium, and platinum.

4. The catalyst precursor according to claim 1, wherein the structure has a plate, mesh, cylindrical, coil or particulate form, or combinations thereof.

5. The catalyst precursor according to claim 1, wherein a plurality of the structures are combined with each other to form a three dimensional structure.

6. A method for using the catalyst precursor comprising immersing the catalyst precursor according to claim 1 in a solution containing a halogenated hydrocarbon compound as a raw material or a part of raw materials to release a catalytically active species from the catalyst precursor.

7. A catalyst precursor comprising a structure surface-treated with a solution containing Caro's acid, wherein the entire structure is composed of gold or a gold-based alloy or at least the surface of the structure is composed of gold or a gold-based alloy, and a catalytic metal compound supported on the surface-treated structure.

8. The catalyst precursor according to claim 7, wherein the solution containing Caro's acid is a solution containing a acid having sulfur as a constituent element and an oxidizer, a solution electrochemically-oxidized the acid having sulfur as a constituent element, or a solution containing a persulfate and sulfuric acid.

9. The catalyst precursor according to claim 7, wherein the surface of the structure treated with the solution on the surface is modified with elemental sulfur, and wherein the catalyst precursor has peaks derived from the catalytic metal compound and also sulfur as analyzed by photoelectron spectroscopy, and wherein the peak derived from sulfur is of the sulfur is orbital observed within a range of 2470 eV±2 eV in terms of the peak top position.

10. The catalyst precursor according to claim 7, wherein the catalytic metal compound is a metal salt or metal complex containing at least one of ruthenium, rhodium, iridium, palladium, and platinum.

11. The catalyst precursor according to claim 7, wherein the structure has a plate, mesh, cylindrical, coil or particulate form, or combinations thereof.

12. The catalyst precursor according to claim 7, wherein a plurality of the structures are combined with each other to form a three dimensional structure.

* * * * *